United States Patent [19]

Head et al.

[11] Patent Number: 4,618,628

[45] Date of Patent: Oct. 21, 1986

[54] CATALYTIC PROCESS

[75] Inventors: Robert A. Head, Chester; Robin Whyman, Christleton Nr Chester, both of England

[73] Assignee: Imperial Chemical Industries PLC, London, England

[21] Appl. No.: 680,660

[22] Filed: Dec. 12, 1984

Related U.S. Application Data

[63] Continuation of Ser. No. 485,455, Apr. 15, 1983, abandoned.

[30] Foreign Application Priority Data

Apr. 15, 1982 [GB] United Kingdom ................ 8211002
Jan. 1, 1983 [GB] United Kingdom ................ 8301005

[51] Int. Cl.$^4$ ............................................. C07C 27/06
[52] U.S. Cl. .................................................. 518/700
[58] Field of Search ........................................ 518/700

[56] References Cited

U.S. PATENT DOCUMENTS

4,362,821 12/1982 Lin .
4,421,862 12/1983 Bradley .

FOREIGN PATENT DOCUMENTS

0013008 7/1980 European Pat. Off. .
0033425 8/1981 European Pat. Off. .
2074164 10/1981 United Kingdom .

*Primary Examiner*—Howard T. Mars
*Attorney, Agent, or Firm*—Cushman, Darby & Cushman

[57] ABSTRACT

A method for the selective, direct preparation of ethanol which comprises contacting a mixture of carbon monoxide and hydrogen at a temperature of from 100° to 400° C. and at a pressure of from 50 to 1000 bars with a catalyst comprising ruthenium and at least one other metal selected from Groups VII and VIII of the Periodic Table and a source of halide ions in a liquid medium comprising an aprotic amide or imide or an aprotic heterocyclic compound containing an —OCO— grouping in the ring.

11 Claims, No Drawings

CATALYTIC PROCESS

This is a continuation of application Ser. No. 485,455, filed Apr. 15, 1983, now abandoned.

This invention relates to a catalytic process and more particularly to a catalytic process for the selective direct production of ethanol from synthesis gas.

The catalytic conversion of synthesis gas (a mixture of carbon monoxide and hydrogen) to useful organic materials is well known. In particular, methanol has been commercially manufactured from synthesis gas by a heterogeneous catalytic reaction for many years. More recently, motivated largely by the increase in the price of oil, processes have been proposed with the object of producing not methanol but organic compounds having two or more carbon atoms in the molecule. All of the processes that have been proposed produce a mixture of products, the constitution of this mixture varying considerably depending on the specific catalyst employed and also on the other reaction variables (temperature, pressure presence of co-catalyst, nature of reaction medium etc). In the majority of these processes, the catalyst contains a metal of Group VIII of the Periodic Table and the products obtained have included methanol, ethanol, propanol, higher alcohols (up to at least $C_{27}$ products), ethylene glycol, propylene glycol, glycerol, ethers and esters of these alcohols, acetaldehyde and acetic acid. Several processes have had the specific object of increasing the proportion of ethylene glycol and/or ethanol in the reaction product at the expense of less valuable materials.

The overall picture presented by the various prior art documents is complex because of the interdependence of the several reaction parameters. It therefore becomes extremely difficult to predict how the reaction will be affected by changing the catalyst composition or reaction conditions.

A detailed review of the prior art is given in European Patent Application No. 13008A which then describes a process for selectively making methanol, ethylene glycol and ethanol, or carboxylate derivatives thereof by reacting hydrogen and carbon monoxide in a suitable solvent in the presence of a solubilised ruthenium carbonyl complex at a temperature between 50° C. and 400° C. and a pressure between 500 psia (34.5 bars) and 15000 psia (1035 bars). The process is preferably carried out in the presence of a promoter or co-catalyst and a wide range of "Lewis Bases" are suggested as promoters including amines, alkanolamines, heterocyclic bases, acyl compounds and hydroxides and salts of various metals. The salts mentioned include carboxylates, halides, carbonates, bicarbonates, sulphates and bisulphates of alkali metals, alkaline earth metals and other metals. Alkali metal halides, particularly iodides are said to allow repeated use of the ruthenium carbonyl complex and are used in many of the Examples. Promoters in general and the difficulties associated with their selection are discussed at some length in the European application, it being pointed out that any Lewis base may be a promoter but all Lewis bases will not serve to act as a promoter under any given set of reaction conditions. It is further pointed out that in most cases a degree of selection between the choice of Lewis base, the amount of ruthenium, the choice of solvent and the reaction parameters will be required to obtain the level of productivity sought.

The aforesaid European Patent Application No. 13008A also discusses reaction solvents in detail stating that the choice of solvent in any particular case can be a complex decision. The preferred solvents are polar compounds and include water, ketones, lactones, carboxylic acids, amides, sulphones, sulphoxides, ethers, halogenated hydrocarbons and polyols.

In all except a very small number of the 38 Examples of the European application, the predominant product is methanol which in most cases far exceeds the total amounts of ethylene glycol and ethanol. In several Examples, no recovery of ethanol is reported and in those cases where ethanol is obtained, the amount is usually very small compared with the amount of methanol. In only 11 Examples does the weight of ethanol produced exceed 30% of the weight of methanol and these Examples usually involve the use of somewhat higher reaction temperatures and/or higher concentrations of ruthenium and/or promoter.

A ruthenium carbonyl complex is employed throughout as the sole source of Group VIII metal except in Example 73 where the reaction mixture additionally contains dicobalt octacarbonyl and uses lithium iodide as promoter and sulpholane as solvent. By comparison with Example 62 which uses an identical formulation except for the cobalt complex, the effect of the cobalt in Example 73 is to lower the reaction rate, methanol again being the major product.

Another ruthenium catalysed system is described in UK Patent Application No. GB 2074164A, the promoter in this case being a halide with a stated preference for chloride and bromide. The preferred solvents are aprotic organic amides. In most of the Examples of this application, the amount of ethanol recovered is much less than the amount of methanol. The only exceptions to this occur when rather unusual reaction conditions are employed, for example high catalyst concentrations or low temperatures with consequent low yields of product.

In the process of European Patent Application No. 33425A, ruthenium is used in conjunction with a minor proportion of at least one other Group VIII metal. The co-catalyst is a compound of one or more of the metals of Group IA, IIA or IIB of the Periodic Table or a nitrogen-containing cation and/or base. Metal compounds mentioned include oxides, hydroxides, carbonates, bicarbonates and acetates with a preference for carboxylates when carboxylic acids are employed as reaction media. Compounds based on nitrogen-containing cations and/or bases include salts wherein the anion is hydroxide, nitrate, halide or carboxylate. The solvents mentioned are polar liquids of the usual types with a preference for ethers and carboxylic acids. In most of the Examples of the application, a ruthenium/rhodium combination is employed as catalyst with a metal carboxylate or pyridine type compound as co-catalyst and glacial acetic acid as solvent. The product consists largely of the acetates of methanol, ethanol and ethylene glycol with good selectivity to the glycol acetates at operating pressures of 1450-1550 bars. In all cases, selectivity to ethyl acetate is poor compared with the methyl and glycol acetates.

U.S. Pat. No. 4,301,253 describes a process for the selective, direct production of ethanol using a ruthenium catalyst and a halogen or halide promoter but a somewhat unconventional solvent, a phosphine oxide.

Additionally, it is known to prepare ethanol by the homologation reaction whereby methanol is reacted with synthesis gas. Processes of this type are reviewed in the aforementioned U.S. Patent.

It has now been found that ethanol can be produced in excellent selectivity direct from synthesis gas using a catalyst based on ruthenium, a halide promoter and selected solvents as hereinafter described.

Thus, according to the invention, there is provided a method for the selective, direct preparation of ethanol which comprises contacting a mixture of carbon monoxide and hydrogen at a temperature of from 100° to 400° C. and at a pressure of from 50 to 1000 bars with a catalyst comprising ruthenium and at least one other metal selected from Groups VII and VIII of the Periodic Table and a source of halide ions in a liquid medium comprising an aprotic amide or imide or an aprotic heterocyclic compound containing an —O—CO— grouping in the ring.

It is a surprising feature of the invention that ethanol is obtained in excellent selectivity using the aprotic reaction media described above whilst the replacement of these media by other known reaction media, for example tetraglyme, pyridine, sulpholane or tetrahydrofuran under the same conditions results in a low (sometimes negligible) reaction rate and/or low ethanol selectivity.

Aprotic amides which may be employed as reaction media in accordance with the present invention include heterocyclic compounds in which the ring contains a group of the formula:

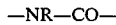

—NR—CO— wherein R is a hydrocarbyl radical. Such compounds include in particular saturated 5- to 7-membered ring compounds, often known as lactams, such as the N-alkyl pyrrolidones and piperidones, for example N-methylpyrrolidone (that is to say 1-methyl-2-pyrrolidinone) and N-methylpiperidone. Other cyclic amides which may be used include N-benzylpyrrolidone, N-alkyl oxindoles and N,N'-dialkyl 2-imidazolidones. Other aprotic amides which may be use include amides in which the nitrogen atom forms part of a heterocyclic ring or carries two hydrocarbyl substituents. As examples of such amides there may be mentioned N-acyl pyrrolidines, piperidines and morpholines and dialkyl amides such as dimethyl-acetamide.

Aprotic imides which may be used in the method of the invention include the N-hydrocarbyl (especially N-alkyl) imides of dicarboxylic acids such as succinic, glutaric and phthalic acids, for example N-methylsuccinimide.

Aprotic heterocyclic compounds containing an —O—CO— grouping which may be used in the method of the invention include lactones, for example γ-butyrolactone, and the anhydrides of dicarboxylic acids such as succinic, methylsuccinic and glutaric acids.

If desired, mixtures of two or more of the said reaction media may be employed, for example a mixture containing N-methylpyrrolidone and γ-butyrolactone.

It is a further surprising feature of the invention that the reaction media described herein, that is to say aprotic amides, imides, lactones and acid anhydrides, are remarkably effective in terms of reaction rate and ethanol selectivity when used in admixture with other aprotic liquid media which, as mentioned above are relatively ineffective when used alone. In some cases, such mixtures result in a higher reaction rate and better ethanol selectivity than do the amides, imides, lactones or anhydrides alone. Such mixtures should contain at least 5%, preferably at least 10%, by weight of aprotic amide, imide, lactone or anhydride, the remainder of the mixture being another aprotic liquid such as an ether, ester, ketone, sulphone or sulphoxide. Mixtures of N-methylpyrrolidone, γ-butyrolactone or methylsuccinic anhydride with ethers such as tetraglyme are particularly effective.

It will be understood that the metals of Group VIII of the Periodic Table additional to ruthenium are iron, cobalt, nickel, rhodium, palladium, osmium, iridium and platinum and the metals of Group VII are manganese and rhenium. In the method of the invention, these metals and ruthenium may be used in elemental form or in the form of their compounds, for example complexes such as carbonyls or salts. Ruthenium is conveniently introduced into the reaction mixture in the form of triruthenium dodecacarbonyl and the other metals may also be introduced as carbonyls.

The total amount of the Group VIII/VII metals used in the method of the invention is not critical and may vary over a wide range. In general, the amount used is at least a catalytic amount, that is to say an amount to provide an acceptable reaction rate. The ratio of one metal to another is again not critical and the optimum ratio may vary to some extent depending upon the particular metals used. In general, mixtures of metals are used containing at least 1%, preferably at least 5%, of each metal on an atomic basis.

In addition to the catalyst, the reaction mixture contains a source of halide ions. For this purpose, the reaction mixture may contain hydrohalic acids or salts thereof, especially alkali metal halides but other halides can be used, for example quaternary ammonium halides. Preferred alkali metal halides are those of lithium, sodium and potassium and useful halide ions include chloride, bromide and especially iodide ions but because of the above mentioned interdependence of the reaction parameters, the effectiveness of any particular cation or anion may vary widely depending upon other reaction conditions. The molar ratio of halide to ruthenium and other Group VIII/VII metals is not critical and is suitably within the range 0.05:1 to 100:1, preferably 0:1:1 to 10:1. If desired, other known promoters, for example crown ethers, may be used in addition to the halide.

The proportion by weight of aprotic liquid medium to catalyst is suitably in the range of 10:1 to 1000:1, preferably 20:1 to 200:1.

The molar ratio of carbon monoxide to hydrogen may suitably be in the range 1:5 to 5:1, especially about 1:1. The reaction may also be carried out in the presence of gaseous inert diluents, for example carbon dioxide.

Preferred reaction temperatures are in the range 150°-300° C., especially 175°-275° C. Preferred reaction pressures are in the range 400 to 1000 bars.

The process may be operated in a continuous or batchwise manner. It may also be carried out in either a homogeneous or a heterogeneous reaction system, the former being preferred. Accordingly, the catalyst may be present in the system as a heterogeneous phase for example as a metal or compound deposited on a solid support such as carbon, silica or alumina or may be dissolved in the liquid medium and thus form a homogeneous phase therewith. If a heterogeneous catalyst is used, the components of the reaction mixture can be separated from each other and from the catalyst by conventional means, for example separating the catalyst by filtration and fractionally distilling the organic components in the mixture. When a homogeneous system is used, the catalyst will remain in the residue after volatile products have been distilled out, collected and separated. The catalyst may be re-used by regeneration of suitable compounds and with fresh addition of the liquid medium.

Conveniently, the catalyst may be immersed in the medium in an autoclave pressurised to the required high pressure and the mixture of reactant gases carbon monoxide and hydrogen passed into the liquid medium. The temperature may be raised as required and maintained for the period of the reaction after which both temperature and pressure are lowered and the product mixture removed from the autoclave. The organic liquid products may be used as a total mixture or may be separated by distillation and the catalyst recovered for re-use if required. Some catalyst is inevitably lost and therefore in large scale operation the initial cost of the metals used in the preparation of the catalyst is important to the economics of the process.

In addition to ethanol, the total reaction product commonly contains one or more other alkanols, for example methanol, n-propanol, n-butanol and n-pentanol as well as compounds such as acetaldehyde, methyl formate, methyl acetate, ethyl formate, ethyl acetate, propyl acetate, ethylene glycol and 2-methyldioxalan. The quantities in which the various compounds occur depends upon the particular catalyst combination used, the promoter, the solvent and the reaction temperature and pressure.

The invention is illustrated but not limited by the following Examples.

EXAMPLES

The following procedure is typical of that used in the Examples recorded in the following Tables.

Reaction pressures were maintained either by the use of manual valves or by air-operated valves controlled by a microcomputer.

Triruthenium dodecacarbonyl (0.850 g, 4 m moles), dicobalt octacarbonyl (0.259 g, 1.5 m moles), potassium iodide (2.0 g, 12 m moles), tetraglyme (40 ml) and N-methylpyrrolidone (10 ml) were charged into a steel autoclave of ca. 120 ml capacity fitted with a flip-flop stirrer. The autoclave was sealed and after being purged with $CO/H_2$ was pressurised to ca. 450 bars with synthesis gas in a 1:1 ratio of CO to $H_2$. The vessel was then heated to 220° C. by means of a heater coil at which point the pressure inside the vessel had risen to ca. 650 bars. The pressure was increased to 850 bars with $CO/H_2$ of the same composition and maintained at 850±50 bars for 4 hours before being allowed to cool to ambient temperature. The autoclave was carefully vented and discharged to give 66.7 gm of material which corresponded to a weight increase of 13.0 gm. Analysis of the products was carried out by gas chromatography using a Porapak Q column.

The Tables show the effect on the composition of the product of variations in catalyst, promoter, solvent, temperature and pressure.

In Table 1, Examples 1-10 are not illustrative of the invention but are included for the purpose of comparison. These Examples show the general ineffectiveness of Group VIII metals other than ruthenium and rhodium in a single-metal system containing potassium iodide as promoter and tetraglyme/N-methylpyrrolidone as solvent. Examples 11-27 show the beneficial effect on ethanol (and n-propanol) production of having a second metal present in addition to ruthenium.

In Table 2, Examples 28, 29, 35-42, 44 and 49 are not illustrative of the invention but are included for the purpose of comparison. The Table shows the beneficial effect on reaction rate and/or ethanol selectivity of using a solvent as required by the invention either alone or in admixture with another solvent. By contrast, other conventional solvents e.g. tetraglyme, sulpholane and tetrahydrofuran allow little reaction and very low ethanol production. The Table also shows that the presence of cobalt in addition to ruthenium has a beneficial effect when N-methylpyrrolidone or butyrolactone are employed as solvents whilst having little or no significant effect when tetraglyme, sulpholane, butyl butanoate or tetrahydrofuran are used.

Table 3 shows the effect of pressure variations on reaction mixtures containing ruthenium/cobalt as catalyst, sodium iodide as promoter and tetraglyme/N-methylpyrrolidone as solvent.

In Table 4, Example 60 is not illustrative of the invention and is included for the purpose of comparison. Examples 55-59 show the effects produced by the various alkali metal iodides whilst Examples 61-65 show the use of the various potassium halides and Examples 66-68 show the use of quaternary ammonium halides.

TABLE 1[a]

| Example | $Ru_3(CO)_{12}$ (gm) | Co-catalyst | (weight) | Rate of alcohol formation (gm/liter/hr) | | | |
|---|---|---|---|---|---|---|---|
| | | | | MeOH | EtOH | $Pr^nOH$ | 1,2-Ethanediol |
| 1 | — | $Rh_4(CO)_{12}$ | 0.279 | 9.4 | 2.28 | 0.1 | 15.52 |
| 2 | 0.851 | — | — | 23.8 | 6.8 | 0.88 | 2.76 |
| 3[b] | 0.848 | — | — | 52.0 | 14.8 | 1.28 | 7.6 |
| 4 | 0.214 | — | — | 28.0 | 4.8 | 0.32 | 4.0 |
| 5[c] | — | $Rh(CO)_2acac$ | 0.386 | 4.8 | 0.72 | 0.05 | 4.8 |
| 6 | — | $Co_2(CO)_8$ | 0.255 | trace | trace | trace | trace |
| 7[b] | — | $Ni(OAc)_2$ | 0.376 | trace | trace | trace | trace |
| 8 | — | $Fe_2(CO)_9$ | 0.273 | trace | trace | trace | trace |
| 9[b] | — | $Mn_2(CO)_{10}$ | 0.295 | trace | trace | trace | trace |
| 10[b] | — | $Pd(OAc)_2$ | 0.337 | trace | trace | trace | trace |
| 11[b] | 0.849 | $Rh_4(CO)_{12}$ | 0.279 | 20.4 | 17.2 | 1.68 | 34 |
| 12 | 0.849 | $Rh_4(CO)_{12}$ | 0.280 | 17.2 | 17.2 | 2.16 | 20.8 |
| 13[c] | 0.853 | $Rh(CO)_2acac$ | 0.387 | 14.0 | 8.4 | 0.68 | 8.4 |
| 14 | 0.850 | $Co_2(CO)_8$ | 0.259 | 17.2 | 27.2 | 3.6 | 7.6 |
| 15 | 0.852 | $Co_2(CO)_8$ | 0.260 | 18.4 | 30.4 | 4.4 | 9.2 |
| 16[c] | 0.853 | $Co_2(CO)_8$ | 0.257 | 18.0 | 15.6 | 2.44 | 0.64 |
| 17[c] | 0.214 | $Co_2(CO)_8$ | 0.065 | 14.4 | 3.56 | 2.4 | trace |
| 18[b] | 0.853 | $Fe_2(CO)_9$ | 0.271 | 48.8 | 16.8 | 1.2 | 4.0 |
| 19[b] | 0.853 | $Mn_2(CO)_{10}$ | 0.293 | 40.8 | 24.4 | 1.36 | 4.8 |
| 20[b] | 0.851 | $Ni(OAc)_2$ | 0.375 | 52.0 | 22.8 | 1.08 | 5.2 |

TABLE 1[a]-continued

| Example | $Ru_3(CO)_{12}$ (gm) | Co-catalyst | (weight) | Rate of alcohol formation (gm/liter/hr) | | | |
|---|---|---|---|---|---|---|---|
| | | | | MeOH | EtOH | $Pr^nOH$ | 1,2-Ethanediol |
| 21[b] | 0.852 | $Pd(OAc)_2$ | 0.337 | 40.0 | 17.2 | 1.08 | 4.0 |
| 22 | 0.213 | $Co_2(CO)_8$ | 0.020 | 28.8 | 7.6 | 0.72 | 6.0 |
| 23 | 0.213 | $Co_2(CO)_8$ | 0.087 | 29.6 | 12.8 | 1.72 | 6.0 |
| 24 | 0.213 | $Co_2(CO)_8$ | 0.173 | 20.4 | 11.6 | 2.0 | 6.0 |
| 25 | 0.213 | $Co_2(CO)_8$ | 0.343 | 19.2 | 23.2 | 7.2 | 4.4 |
| 26 | 0.213 | $Co_2(CO)_8$ | 0.855 | 5.6 | 29.2 | 14.4 | 4.8 |
| 27 | 0.213 | $Co_2(CO)_8$ | 1.712 | 0.12 | 34.8 | 16.0 | 5.6 |

[a]Unless otherwise stated all reactions were carried out at 850 atmospheres pressure of $CO/H_2$ (1:1 ratio) and at 220° C. for 4 hours. Potassium iodide (2 g) was added as promoter and tetraglyme/N—methylpyrrolidone (4:1 v/v ratio) was used as solvent.
[b]Reaction was carried out for 2 hours.
[c]Reaction was carried out at 500 atmospheres $CO/H_2$ (1:1 ratio).

TABLE 2[a]

| Example | Solvent Composition | Rate of alcohol formation (gm/liter/hr) | | | |
|---|---|---|---|---|---|
| | | MeOH | EtOH | $Pr^nOH$ | 1,2-Ethanediol |
| 28[b] | Tetraglyme (100%) | 2.84 | trace | trace | trace |
| 29 | Tetraglyme (100%) | 4.8 | 1.4 | 0.12 | 0.12 |
| 30 | Tetraglyme (95%), NMP (5%)[c] | 8.48 | 3.68 | 0.36 | 0.2 |
| 31 | Tetraglyme (90%), NMP (10%)[c] | 12.72 | 5.16 | 0.48 | 0.4 |
| 32 | Tetraglyme (85%), NMP (15%)[c] | 18.36 | 8.04 | 0.60 | 0.52 |
| 33 | Tetraglyme (50%), NMP (50%)[c] | 32.56 | 19.44 | 0.88 | 0.48 |
| 34 | NMP (100%)[c] | 24.04 | 7.84 | 0.36 | 0.12 |
| 35[b] | NMP (100%)[c] | 13.6 | 1.76 | 0.16 | 2.0 |
| 36[b] | Sulpholane (100%) | 9.6 | 1.08 | 0.32 | 0.32 |
| 37 | Sulpholane (100%) | 2.8 | trace | trace | trace |
| 38[b] | Butylbutanoate (100%) | trace | trace | trace | trace |
| 39 | Butylbutanoate (100%) | trace | trace | trace | trace |
| 40[b] | Tetrahydrofuran (100%) | 0.52 | trace | trace | trace |
| 41 | Tetrahydrofuran (100%) | 0.96 | 0.24 | trace | trace |
| 42[b] | γ-butyrolactone (100%) | 13.6 | 8.2 | 0.4 | 9.7 |
| 43 | γ-butyrolactone (100%) | 16.0 | 12.4 | 1.32 | 2.72 |
| 44 | Tetraglyme (80%), Pyridine (20%) | 6.0 | 2.4 | trace | trace |
| 45 | Sulpholane (80%), NMP (20%)[c] | 13.6 | 2.8 | 0.32 | 0.72 |
| 46 | Tetraglyme (80%), Me—succinicanhydride (20%) | 2.12 | 5.8 | 0.88 | 0.44 |
| 47 | Tetraglyme (80%), NCP (20%)[d] | 18.0 | 6.0 | 0.56 | 4.0 |
| 48 | Tetraglyme (80%), N—methylpiperidone (20%) | 22.4 | 11.2 | 0.80 | 1.92 |
| 49 | Tetraglyme (80%); N—ethylpiperidine (20%) | trace | trace | trace | trace |
| 50 | Tetraglyme (80%), γ-butyrolactone (20%) | 20.0 | 10.8 | 0.4 | 1.4 |

[a]Unless otherwise stated, all reactions were carried out at 850 atmospheres pressure of $CO/H_2$ (1:1 ratio) and at 220° C. for 4 hours. Potassium iodide (2 g) was added as promoter and the catalyst consisted of $Ru_3(CO)_{12}$ (0.214 g) and $Co_2(CO)_8$ (0.066 g). Where a mixture of solvents is used, volume percentages are given.
[b]Catalyst consisted of $Ru_3(CO)_{12}$ (0.213 g) only.
[c]NMP = N—methylpyrrolidone.
[d]NCP = N—cyclohexylpyrrolidone TABLE 3[a]

| Example | Reaction Pressure (ATM)[b] | Reaction Temperature (°C.) | Rate of alcohol formation (cm/liter/hour) | | | |
|---|---|---|---|---|---|---|
| | | | MeOH | EtOH | $Pr^nOH$ | 1,2-Ethanediol |
| 51 | 1000 | 220 | 18.8 | 27.6 | 2.0 | 10.8 |
| 52 | 500 | 220 | 18.8 | 13.6 | 1.2 | 3.2 |
| 53 | 300 | 220 | 11.8 | 2.56 | 0.32 | trace |
| 54 | 300 | 230 | 18.8 | 6.8 | 1.2 | trace |

[a]All reactions were carried out with $Ru_3(CO)_{12}$ (0.213 g) and $Co_2(CO)_8$ (0.065 g) as catalyst in tetraglyme (80%) N—methylpyrrolidone (20%) as solvent. Sodium iodide (1.8 g) was added as promoter and reactions were carried out for 4 hours.
[b]$CO/H_2$ ratio 1:1.

TABLE 4[a]

| Example | Reaction Pressure (ATM)[b] | Reaction Temperature | Promoter | Promoter Weight (g) | Rate of alcohol formation (gm/liter/hour) | | | |
|---|---|---|---|---|---|---|---|---|
| | | | | | MeOH | EtOH | $Pr^nOH$ | 1,2-Ethanediol |
| 55 | 500 | 230 | LiI | 1.6 | 16.0 | 17.2 | 2.28 | 1.2 |
| 56 | 500 | 230 | NaI | 1.8 | 21.2 | 13.0 | 1.52 | 1.2 |
| 57 | 500 | 230 | KI | 2.0 | 18.4 | 7.2 | 0.76 | 0.8 |
| 58 | 500 | 230 | RBI | 2.5 | 14.8 | 4.8 | 0.52 | 0.8 |

TABLE 4a-continued

| Example | Reaction Pressure (ATM)[b] | Reaction Temperature | Promoter | Promoter Weight (g) | Rate of alcohol formation (gm/liter/hour) | | | |
|---|---|---|---|---|---|---|---|---|
| | | | | | MeOH | EtOH | Pr$^n$OH | 1,2-Ethanediol |
| 59 | 500 | 230 | CsI | 3.1 | 9.2 | 4.4 | 0.48 | 0.8 |
| 60 | 850 | 220 | KOAc | 1.2 | trace | trace | trace | trace |
| 61 | 850 | 220 | KF | 0.7 | trace | trace | trace | trace |
| 62 | 850 | 220 | KCl | 0.9 | trace | trace | trace | trace |
| 63 | 850 | 220 | KBr | 1.43 | 2.8 | 1.2 | 0.04 | trace |
| 64 | 850 | 220 | KBr | 1.43[c] | 6.8 | 4.4 | 0.32 | trace |
| 65 | 850 | 220 | KI | 2.0 | 21.8 | 8.0 | 1.0 | 6.4 |
| 66 | 850 | 220 | Me$_4$NCl | 1.3 | 16.0 | 5.6 | 0.4 | 1.0 |
| 67 | 850 | 220 | Me$_4$NBr | 1.85 | 7.6 | 11.6 | 0.44 | 1.0 |
| 68 | 850 | 220 | Me$_4$NI | 2.4 | 3.2 | 16.8 | 0.28 | 1.04 |

[a]All reactions were carried out with Ru$_3$(CO)$_{12}$ (0.214 g) and Co$_2$(CO)$_8$ (0.066 g) as catalyst in tetraglyme (80%)/N—methyl-pyrrolidone (20%) as solvent for 4 hours.
[b]CO/H$_2$ ratio 1:1
[c]18-Crown-6 (3.2 g) also added.

We claim:

1. A method for the selective, direct preparation of ethanol which comprises contacting a mixture of carbon monoxide and hydrogen at a temperature of from 100° to 400° C. and at a pressure of from 50 to 1000 bars with a catalyst comprising ruthenium and at least one other metal selected from Groups VII and VIII of the Periodic Table and a source of iodide ions in a liquid medium comprising an aprotic amide or imide or an aprotic heterocyclic compound containing an —OCO— grouping in the ring.

2. A method according to claim 1 wherein the liquid medium is or includes a heterocyclic compound having a 5- to 7-membered ring containing a group of the formula:

—NR—CO— wherein R represents a hydrocarbyl radical.

3. A method according to claim 2 wherein the heterocyclic compound is an N-alkylpyrrolidone or N-alkypiperidone.

4. A method according to claim 3 wherein the N-alkylpyrrolidone is N-methylpyrrolidone.

5. A method according to claim 4 wherein the N-methylpyrrolidone is used together with tetraglyme.

6. A method according to claim 1 wherein the liquid medium is or includes γ-butyrolactone.

7. A method according to claim 1 wherein the catalyst comprises ruthenium and at least one of iron, cobalt, nickel, rhodium, palladium and manganese.

8. A method according to claim 1 wherein the catalyst comprises ruthenium and cobalt.

9. A method according to claim 1 wherein the source of halide ions is an alkali metal iodide or quaternary ammonium iodide.

10. A method according to claim 1 wherein the reaction temperature is in the range 175°-275° C.

11. A method according to claim 1 wherein the reaction pressure is in the range 400-1000 bars.